(12) United States Patent
Freeman

(10) Patent No.: US 9,421,389 B2
(45) Date of Patent: Aug. 23, 2016

(54) CPR ASSISTANCE AND EFFECTIVENESS DISPLAY

(75) Inventor: Curtis Freeman, Windham, NH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2247 days.

(21) Appl. No.: 12/278,593

(22) PCT Filed: Feb. 9, 2007

(86) PCT No.: PCT/IB2007/050432
§ 371 (c)(1),
(2), (4) Date: Aug. 7, 2008

(87) PCT Pub. No.: WO2007/093944
PCT Pub. Date: Aug. 23, 2007

(65) Prior Publication Data
US 2009/0024175 A1    Jan. 22, 2009

Related U.S. Application Data

(60) Provisional application No. 60/773,450, filed on Feb. 15, 2006.

(51) Int. Cl.
| A61N 1/39 | (2006.01) |
| A61H 31/00 | (2006.01) |
| G09B 23/28 | (2006.01) |
| G06F 19/00 | (2011.01) |

(52) U.S. Cl.
CPC .............. *A61N 1/3925* (2013.01); *A61H 31/00* (2013.01); *A61N 1/3993* (2013.01); *G06F 19/3481* (2013.01); *G09B 23/288* (2013.01); *A61H 2201/5058* (2013.01); *G06F 19/3406* (2013.01)

(58) Field of Classification Search
CPC ...................................................... A61N 1/3993
USPC ........................................................ 607/1–6
See application file for complete search history.

(56) References Cited

U.S. PATENT DOCUMENTS

| 4,198,963 A | 4/1980 | Barkalow et al. |
| 4,797,104 A | 1/1989 | Laerdal et al. |
| 4,850,876 A | 7/1989 | Lutaenko et al. |
| 4,915,635 A | 4/1990 | Ingenito et al. |
| 5,800,460 A * | 9/1998 | Powers et al. ..................... 607/5 |
| 6,125,299 A * | 9/2000 | Groenke et al. .................. 607/6 |
| 6,306,107 B1 | 10/2001 | Myklebust et al. |
| 6,337,699 B1 * | 1/2002 | Nielsen ......................... 715/837 |
| 6,351,671 B1 * | 2/2002 | Myklebust et al. ............... 607/5 |
| 6,356,785 B1 | 3/2002 | Snyder et al. |
| 6,807,442 B1 * | 10/2004 | Myklebust et al. ........... 600/509 |
| 2005/0137653 A1 * | 6/2005 | Friedman et al. ............... 607/60 |

(Continued)

FOREIGN PATENT DOCUMENTS

| EP | 1057451 A | 4/2009 |
| JP | S6135871 B2 | 8/1986 |

(Continued)

*Primary Examiner* — William Levicky

(57) ABSTRACT

An instrument is described for assisting a rescuer in the proper administration of CPR. A sensor detects movement of the chest caused by ventilation. The sensor signals are processed to produce a control signal representative of the effectiveness of the ventilation. A lung icon is displayed in the outline shape of human lungs and the outline is displayed filled to a level which indicates the effectiveness of the ventilation.

12 Claims, 4 Drawing Sheets

(56) References Cited

U.S. PATENT DOCUMENTS

| | | |
|---|---|---|
| 2005/0197672 A1 | 9/2005 | Freeman |
| 2006/0173501 A1* | 8/2006 | Stickney et al. .................. 607/5 |
| 2009/0024175 A1* | 1/2009 | Freeman .......................... 607/6 |
| 2009/0254138 A1* | 10/2009 | Stahmann ........................ 607/6 |

FOREIGN PATENT DOCUMENTS

| | | |
|---|---|---|
| JP | 63502063 A | 8/1998 |
| JP | 2001037740 A | 2/2001 |
| WO | 2004/058351 A | 7/2004 |
| WO | 2006136974 A2 | 12/2006 |

* cited by examiner

CPR ASSISTANCE AND EFFECTIVENESS DISPLAY

This invention relates to medical instruments designed to assist in the delivery of or gauge the effectiveness of cardiopulmonary resuscitation (CPR) and, in particular, to a display for such instruments.

When a patient is stricken with sudden cardiac arrest, two types of treatment are required: CPR to oxygenate the blood and force a flow of blood through the vascular system, importantly to the brain, and defibrillation to restart the body's automatic electrical stimulation of the heart. Modern automatic external defibrillators (AEDs) and defibrillator/monitors assist the emergency medical technical in providing both types of treatment. Defibrillation can be provided automatically following automated analysis of the ECG waveform or manually by the EMT after observing the ECG waveform on the monitor. The manually controlled instruments such as the Philips MRx defibrillator/monitor when operated manually can also be set to a CPR mode, during which assistance is given in the delivery of CPR and the results of CPR, chest compressions and ventilation, are monitored. Automated instruments such as the MRx defibrillator/monitor when operated in the automatic mode and AEDs from Philips Medical Systems of Andover, Mass. can also execute rescue protocols in which defibrillation shocks and periods of CPR are directed and carried out at appropriate times in accordance with the patient's vital signs. Recent studies have shown that different patients may be resuscitated more effectively with different treatment regimens depending upon various factors. One factor which affects the likelihood of success of defibrillation is the amount of time that has elapsed since the patient experienced the arrhythmia ("downtime"). This research has indicated that, depending on the duration of cardiac arrest, a patient will have a better probability of recovery with one protocol as compared to another. If the AED or defibrillator/monitor is set up for a less effective protocol for the resuscitation of a particular patient, that patient's probability of recovery may be reduced. These studies have shown that some of these patients have a better chance of being resuscitated if CPR is performed first, which will start by providing externally driven circulation and ventilation which may bring the patient to a condition where application of a shock is more likely to be successful at restoring spontaneous circulation. Accordingly, some defibrillators guide the rescuer in the selection of the treatment protocol which experience has dictated will be more effective under the present patient conditions. See, for instance, U.S. patent [application Ser. No. 60/751,269, filed Dec. 16, 2005].

In addition to providing intervals during which CPR is to be performed and helping a rescuer choose the treatment protocol likely to be most effective, more advanced defibrillators such as those mentioned above can guide a rescuer in the proper application of CPR as described in U.S. Pat. No. 6,306,107 (Myklebust et al.) These defibrillators are equipped with a pad or puck which a rescuer places on the chest of the patient and against which the rescuer delivers the chest compressions of CPR. The chest compressions are often applied in synchronism with a rhythmic tone produced by the instrument. Since the depth of chest compressions is the best non-invasive indicator of blood flow, the pad or puck includes an accelerometer which is used to measure the depth of each compression as well as the rate of the compressions. If the accelerometer signals indicate that CPR is being improperly delivered, the defibrillator will issue audible instructions directing the rescuer to "press harder" or to "press faster," thereby guiding the rescuer in the proper delivery of the CPR compressions. In addition to monitoring chest compressions, some of these instruments also monitor ventilation by the changes in the patient's thoracic impedance. If ventilation is being improperly administered the instrument can issue audible instructions to "ventilate more" or "ventilate less" or "faster" or "slower" or "more (or less) forcefully." In addition to these audible cues, it would be further beneficial for the rescuer to be able to observe a visual indication that the CPR being administered is effective.

In accordance with the principles of the present invention, a patient monitor/defibrillator is provided with a display that indicates the effectiveness of CPR. The display includes a graphic which depicts the filling of the lungs with air, a visible indicator of the effectiveness of CPR ventilation. In a constructed patient monitor/defibrillator the display icon is an icon depicting the lungs which are shown on the display to fill or empty in concert with ventilation of the patient. When the rescuer observes the lung icon filling and/or emptying fully, the rescuer is assured that the CPR ventilation is being administered.

In addition to being used with patient monitor/defibrillator instruments, the present invention can be used with CPR training mannequins and like devices and with instruments designed to assist in the delivery of CPR without themselves providing defibrillation.

In the Drawings

Figure 1:
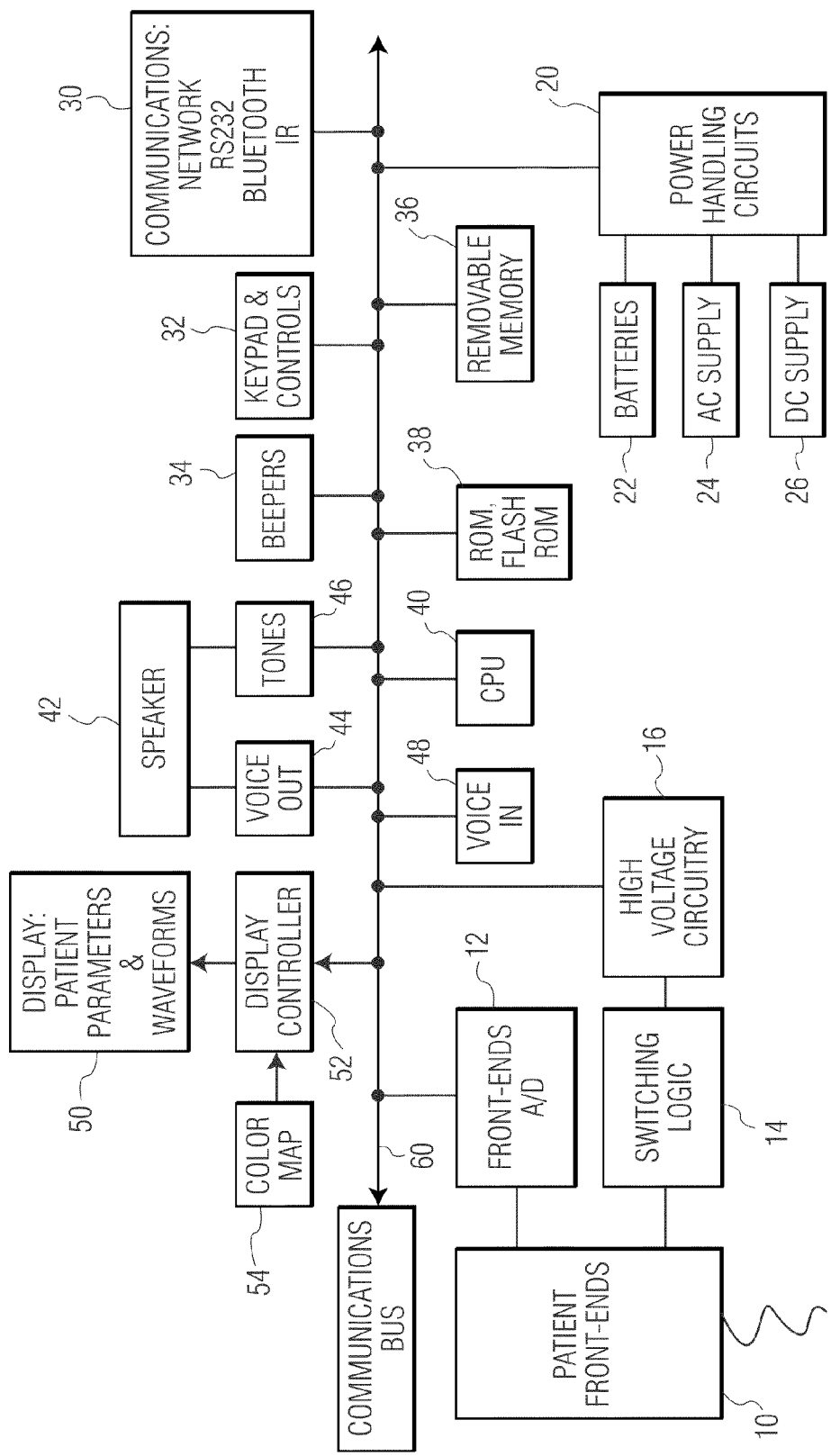
FIG. 1 illustrates in block diagram form a portable patient monitor/defibrillator constructed in accordance with the principles of the present invention.
Figure 2A:
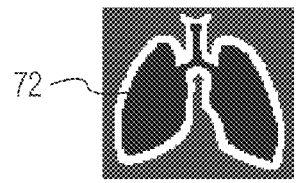
FIGS. 2a-2e illustrate a first example of lung icons designed in accordance with the principles of the present invention.
Figure 2B:
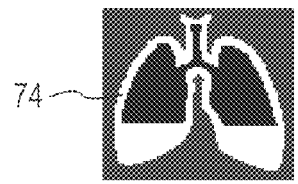
Figure 2C:
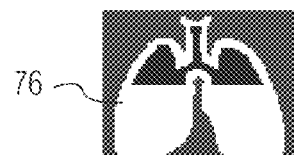
Figure 2D:
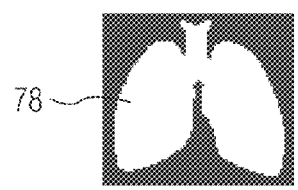
Figure 2E:
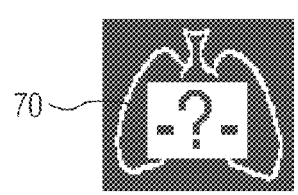

Referring first to FIG. 1, a patient monitor/defibrillator constructed in accordance with the principles of the present invention is shown in block diagram form. The instrument shown in FIG. 1 is capable of performing defibrillation of a patient who is experiencing ventricular fibrillation. It is also capable of performing ECG monitoring including the cardiac monitoring necessary for automatic defibrillation decision-making. The illustrated monitor is also capable of $SpO_2$ oxygen sensing, noninvasive blood pressure monitoring, and end tidal $CO_2$ monitoring. Other functions such as invasive blood pressure monitoring and patient temperature monitoring may also be found in such a multi-functional instrument. In accordance with the present invention, the instrument also guides a rescuer in the proper delivery of CPR.

The monitor/defibrillator has a plurality of patient front-ends, which are input circuitry for the sensors attached to the patient. This circuitry includes conventional sensing and amplification circuitry for ECG electrodes, for optical oxygen sensors, for pressure sensing and for carbon dioxide sensing, among others. In accordance with the present invention, input circuitry is also provided for an accelerometer of a CPR compression sensor which is placed on the patient's chest during application of CPR compressions. The information received by the patient sensors and the front-end circuitry 10 is digitized by front-end A/D converters 12 if the signals are not already in digital form. The digitized information is coupled to processing circuitry of the instrument by a communications bus 60 which connects data between the various modules of the instrument.

The monitor/defibrillator instrument includes high voltage circuitry 16 for defibrillator operation. The high voltage circuitry produces the high voltage pulses necessary for defibrillation which are connected at the appropriate times by switching logic 14 to defibrillator electrodes coupled to the patient. This circuitry provides the high voltage shocks needed to disrupt the ventricular fibrillation and return the heart to a normal rhythm. The shock level and waveform delivered for defibrillation can be automatically calculated by a processor in the monitor or can be manually set with the controls of the instrument by an experienced medical technician or physician.

Power for the modules within the monitor/defibrillator instrument is distributed by power handling circuits 20. The power handling circuits 20 will distribute power from batteries 22, from an AC supply 24, or from a DC supply 26. The AC and DC supplies are also coupled to circuitry which charges the batteries when the monitor is powered from these external power sources.

The information obtained by the instrument may be sent to other instruments or locations by communications circuitry 30. This may include a network connection, an RS232 connection, and/or a wireless connection (e.g. Bluetooth, WiFi or infrared, etc.).

The monitor/defibrillator instrument is operated and adjusted by means of a keypad and controls 32. In a constructed embodiment the keypad is a membrane keypad providing integrity against environmental conditions. Controls such as an on/off switch, power level and shock delivery controls for defibrillation, a printer, and other functions may also be provided.

The monitor/defibrillator is operated under control of a central processing unit (CPU) 40. The CPU runs software stored on a read-only memory (ROM) 38. Flash ROM is also provided for the control of feature setups and new or special capabilities such as waveform information. Removable memory 36 is provided for storage of information generated during a patient episode. Patient information such as cardiac waveforms before and after defibrillation are also stored on the removable memory 36, which can be removed and given to a subsequent care-giver for review, record-keeping, and subsequent diagnosis. The removable memory 36 can also record voice information from a care-giver speaking into a microphone 48.

Beepers 34 are used to drive a solid-state sound source that produces short "chirping" sounds. These sounds indicate that the instrument's resident self-test has detected a low battery level or a malfunction in a patient-critical circuit group. There is also a dedicated display on the front of the instrument that presents a large, flashing, red X to indicate a low battery level or a large, fixed, red X to identify a circuit failure.

Tones 46 are produced by the software and then used to drive the speaker 42. This capability is used during certain monitoring functions such as in the production of a short tone in response to each heart cycle. Combinations of tones are used to issue audible alerts and alarms when a patient's vital measurements fall outside the alarm limits selected. The speaker 42 can reproduce pre-recorded voice instructions and information stored and reproduced from voice out circuitry 44.

In accordance with the principles of the present invention a display 50 is provided for the display of patient parameters and waveforms as discussed more particularly below. The information to be displayed is provided by the CPU to a display controller 52 which provides the necessary drive signals for display of information on the display. In a constructed embodiment the display is a color LCD display, although other types of displays such as a CRT display may be used in a particular embodiment. The display controller 52 displays information in accordance with a color map provided by color map store 54. In a constructed embodiment the color map is stored in tabular form. In other embodiments the color map may be stored as an algorithm or other programmed information.

FIGS. 2a-2e illustrate a first set of example lung icons as displayed on a monitor/defibrillator constructed in accordance with the present invention. In these examples each icon is seen to depict a pair of lungs connected to the trachea. The degree to which the lungs are "filled," in these examples by a white color, indicates the volume of air or other gas in the lungs. Alternatively the degree to which the lungs in the icon are filled may depict the effectiveness of CPR, with fuller lungs indicating more effective CPR ventilation. The icons can be shown as a sequence of discretely differently filled lung icons in a row or group. For instance, the lung icons 72, 74, 76, 78 can be displayed in a row, and the icon which best illustrated the condition of the lungs is highlighted or illuminated. Another example is a single lung icon graphic with the shading in the lungs dynamically changed to matched the sensed condition of the patient or CPR. The sensed condition is used to determine the degree to which the lungs should be displayed as being filled, and the fill shading or brightening is added accordingly. The lungs can be displayed to fill in one or only a few discrete steps, or can be displayed to fill and empty in a continuous motion in real time.

There can be times when the correct volume representation to display may be uncertain. This may be the case when the CPR ventilation is initially starting or when the data needed to derive the icon filling is inadequate or erroneous. In such cases the lung icon can display a unique characteristic such as the question mark symbol of the icon 70 in FIG. 2e.

Figure 3A:
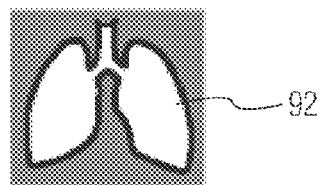
FIGS. 3a-3d illustrate a second example of lung icons designed in accordance with the principles of the present invention.
Figure 3B:
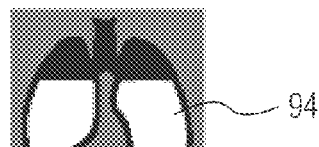
Figure 3C:
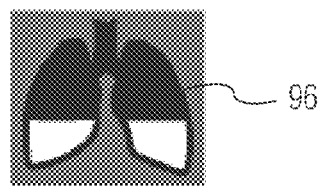
Figure 3D:
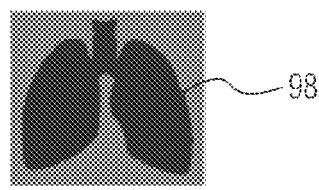

FIGS. 3a-3d illustrate a second example of lung icons in accordance with the principles of the present invention. In this example the lung icon 92 is illustrated as white-filled when the lungs are being represented as empty as shown in FIG. 3a. When the lungs are represented as one-third filled they appear as shown by icon 94 in FIG. 3b, in which the upper one-third of the lungs are shown filled with a dark color which may be the same shade or color as the lung outline. In FIG. 3c the darker color or shade is seen to occupy two-thirds of the icon 96 when the lungs are two-thirds inflated. When the lungs are completely inflated the icon appears as shown by icon 98 in FIG. 3d.

Figure 4:
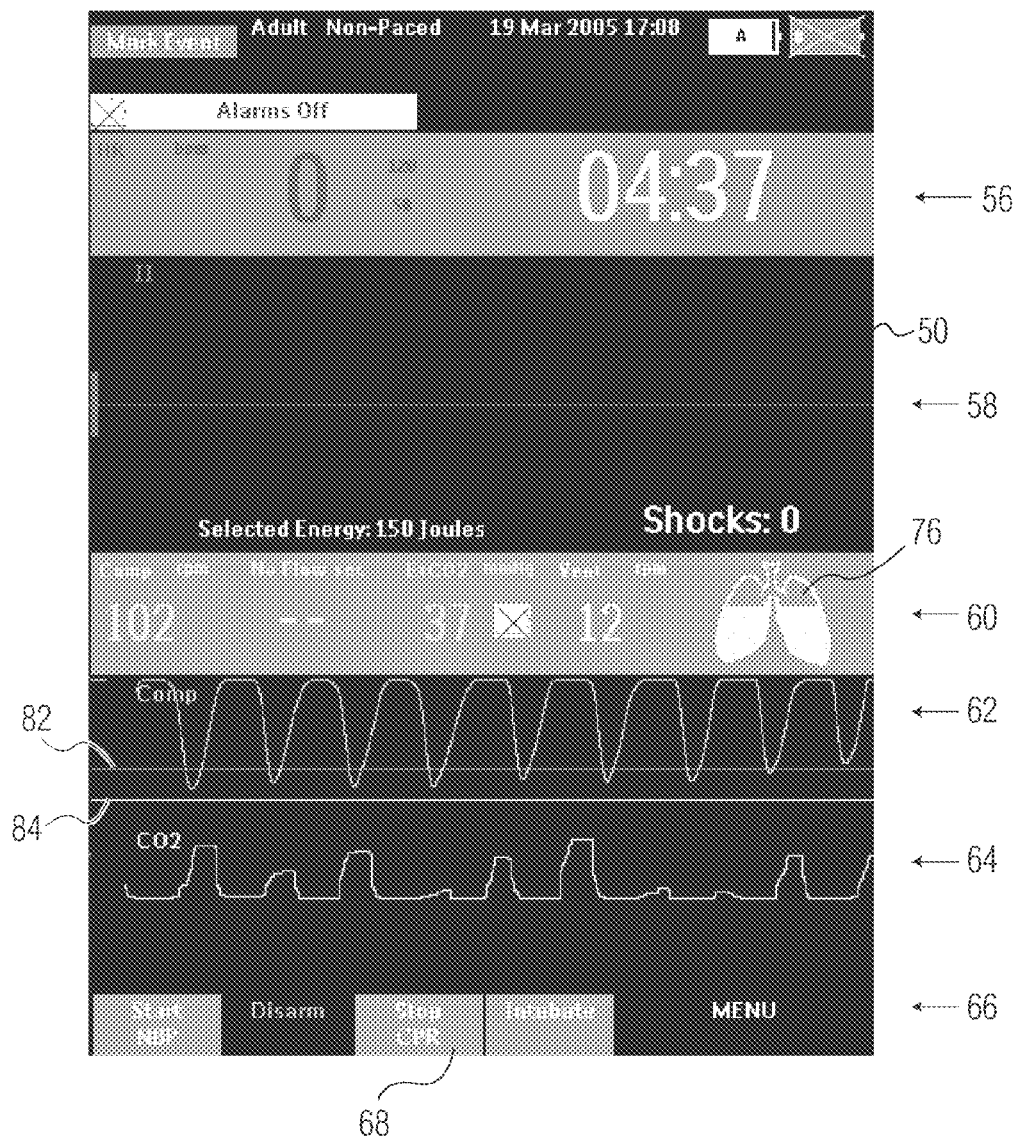
FIG. 4 illustrates a patient monitor/defibrillator CPR display showing a lung icon of the present invention.

FIG. 4 illustrates a display 50 from a constructed defibrillator/monitor in accordance with the principles of the present invention. At the top of the display 50 is a display field 56 in which the patient's heart rate is displayed in beats per minute. To the right of the heartbeat display is a clock which can display real or elapsed time. The display field 58 is used to display the patient's ECG waveform. Defibrillator information, the current energy level setting and the number of shocks delivered, is displayed at the bottom of this field 58.

The next field 60 displays information about CPR when the instrument is operating in the CPR mode. In this example there are three ways to enter the CPR mode. One is to press the softkey 68 at the bottom of the display. In a touchscreen implementation this can be done by touching the softkey 68 on the display. When the "Start CPR" softkey is touched, it changes to a "Stop CPR" control key as shown in FIG. 4. In other implementations a row of buttons can be located immediately below the row of softkeys and a function is actuated by pressing the button below the appropriate softkey. Another way to enter the CPR mode is automatically when the defibrillator/monitor is executing a treatment protocol and operating automatically. A third way to enter the CPR mode is for the rescuer to begin chest compressions using the pad or compression sensor connected to the instrument. When the instrument senses the reception of compression signals from the pad or compression sensor, the instrument will immediately enter the CPR mode to monitor and assist the administration of CPR.

As the rescuer administers chest compressions the defibrillator/monitor may produce a metronome tone at the proper rate for CPR. The actual rate of the compressions as sensed by the accelerometer is displayed as a "Comp" (compressions) number in the display area 60, in this example, 102 compressions per minute. The depth of the chest compressions is illustrated graphically in the display area 62. This graphic curve is normally at the top of the area but pulses downward toward lines 82 and 84 when a chest compression is applied to the patient. When the compression is of a depth which satisfies the American Heart Association CPR standard, the downward peak of the pulse is located between the two lines, thereby giving the rescuer a visual indication of the effectiveness of the applied chest compressions.

To the right of the compression number in display area 60 is a "No Flow" timer which begins counting seconds if the CPR chest compressions stop or are interrupted, thereby marking the elapsed time since the cessation of the compressions.

In accordance with the present invention ventilation information is shown on the right side of the display area 60. The ventilation or respiration rate is numerically shown in this area. In this example the respiration rate is shown as 12 respirations per minute. To the right of the respiration rate is a lung icon 76, which is displaying the lungs as partially filled in this example. The CPU 40 of the defibrillator/monitor of this example executes a ventilation algorithm to produce the ventilation displays. This particular ventilation algorithm receives a patient impedance signal from electrodes attached to the chest of the patient, such as ECG or defibrillation electrodes. As is well known, the patient's chest impedance can be measured by applying a small voltage signal to such electrodes and then measuring the response or attenuation of the small voltage signal by the body of the patient. As the patient's chest is inflated and deflated by ventilation the chest will expand and relax and this motion will change the chest impedance. The changing chest impedance is thus an indicator of ventilation. Ventilation for CPR can be provided in numerous ways, including mouth-to-mouth, by a mechanical ventilator, or a bag mask, and with the patient intubated or not intubated with an endotracial tube. A softkey at the bottom of the display is depressed by the rescuer when the patient is intubated, causing a change of the ventilation limits allowable by the ventilation algorithm. When the ventilation algorithm determines that ventilation is proceeding properly, a mostly or completely full lung icon 76 is displayed, and when ventilation is not being administered as required a partially full or empty lung icon is shown. In a situation where the volume of air in the lungs was quantitatively known, a volume parameter could control the degree of filling shown by the displayed chest icon.

The display area 64 at the bottom of the display 50 graphically shows the measurement of entidal $CO_2$ when a $CO_2$ sensor is affixed to the patient.

Other symbols of an object which can be displayed as full or empty can also be used. A simple embodiment is a circle which is filled in when the lungs are full or are being properly filled, and is shown empty when the lungs are empty of air or are being improperly filled. A lung icon of the present invention can be used with other medical devices which interact with the lungs or breathing such as a plethysmograph.

What is claimed is:

1. An instrument which assists a rescuer in the administration of CPR comprising:
   a sensor which operates to sense an effect of ventilation and produce output signals indicative of the ventilation;
   a processor, responsive to the sensor output signals, which produces a control signal which represents the effectiveness of the ventilation including displacement; and
   a display which may be viewed by an administrator of CPR and comprises a lung icon illustrating the effectiveness of the ventilation by the degree to which the lung icon is displayed as filled,
   wherein the lung icon is displayed as filled to a degree which is in relation to displacement.

2. The instrument of claim 1, wherein the sensor comprises an electrode responsive to chest impedance.

3. The instrument of claim 1, wherein the sensor further comprises a force sensor responsive to chest compressions and wherein the processor produces a control signal which represents the force of applied chest compressions,
   wherein the display further comprises a display of the effectiveness of the chest compressions.

4. The instrument of claim 1, wherein the lung icon further comprises an outline illustration of the anatomy of human lungs,
   wherein the outline illustration is displayed as filled to a degree set by the control signal.

5. The instrument of claim 1, wherein the lung icon further comprises a plurality of outline illustrations of the anatomy of human lungs, each of which is displayed as filled to a different degree,
   wherein one of the outline illustrations is highlighted in response to the control signal.

6. The instrument of claim 1, wherein the lung icon further comprises an outline illustration of a predetermined shape,
   wherein the outline illustration is displayed as filled to a degree set by the control signal.

7. The instrument of claim 1, wherein the control signal is further indicative of the inability to represent the effectiveness of the ventilation,
   wherein the lung icon further illustrates that ventilation effectiveness is indeterminate.

8. The instrument of claim 1, further comprising:
   a pair of defibrillator electrodes which senses a patient ECG signal and is capable of delivering a defibrillation shock;
   a shock delivery circuit responsive to the processor and coupled to the defibrillator electrodes,
   wherein the processor is responsive to the patient ECG signals for determining whether a shock should be delivered by the shock delivery circuit; and
   wherein the defibrillator electrodes and processor are operable to measure chest impedance.

9. The instrument of claim 8, further comprising a rescue protocol which is executable by the processor,
   wherein the rescue protocol causes the instrument to be operated in a first mode during which a defibrillation shock may be delivered and a second mode during which CPR may be performed and the lung icon displayed.

10. The instrument of claim 8, wherein the instrument is further operable to train the rescuer in the proper administration of CPR.

11. The instrument of claim 1, wherein the instrument is further operable to train the rescuer in the proper administration of CPR.

12. The instrument of claim 11, wherein the instrument is further operable to guide the rescuer in the proper administration of CPR during a rescue.

\* \* \* \* \*